United States Patent
Orlowski

(10) Patent No.: US 8,257,424 B2
(45) Date of Patent: Sep. 4, 2012

(54) RADIALLY EXPANDABLE VASCULAR STENT

(75) Inventor: Michael Orlowski, Bonn (DE)

(73) Assignee: Eurocor GmbH, Bonn (DE)

(*) Notice: Subject to any disclaimer, the term of this patent is extended or adjusted under 35 U.S.C. 154(b) by 0 days.

(21) Appl. No.: 10/296,287

(22) PCT Filed: May 18, 2001

(86) PCT No.: PCT/EP01/05736
§ 371 (c)(1), (2), (4) Date: Apr. 30, 2003

(87) PCT Pub. No.: WO01/89414
PCT Pub. Date: Nov. 29, 2001

(65) Prior Publication Data
US 2003/0167084 A1    Sep. 4, 2003

(30) Foreign Application Priority Data
May 22, 2000  (WO) .................. PCT/EP00/04658

(51) Int. Cl.
*A61F 2/82* (2006.01)
(52) U.S. Cl. ..................... 623/1.15; 623/1.16
(58) Field of Classification Search ............ 606/1.15, 606/1.13; 623/1.15, 1.16
See application file for complete search history.

(56) References Cited

U.S. PATENT DOCUMENTS

| | | | | |
|---|---|---|---|---|
| 5,104,404 A | * | 4/1992 | Wolff | 623/1.16 |
| 5,545,208 A | * | 8/1996 | Wolff et al. | 623/1.22 |
| 5,607,442 A | * | 3/1997 | Fischell et al. | 623/1.18 |
| 5,632,772 A | * | 5/1997 | Alcime et al. | 623/1.35 |
| 5,669,932 A | * | 9/1997 | Fischell et al. | 606/198 |
| 5,871,436 A | * | 2/1999 | Eury | 600/3 |
| 6,068,656 A | * | 5/2000 | Von Oepen | 623/1.17 |
| 6,071,308 A | * | 6/2000 | Ballou et al. | 623/1.15 |
| 6,193,744 B1 | * | 2/2001 | Ehr et al. | 623/1.16 |
| 6,217,608 B1 | * | 4/2001 | Penn et al. | 623/1.16 |

(Continued)

FOREIGN PATENT DOCUMENTS

CA    2237466    * 11/1998

(Continued)

OTHER PUBLICATIONS

European International Search Report of PCT/EP01/05736 dated Oct. 24, 2001.

(Continued)

*Primary Examiner* — Thomas J Sweet
*Assistant Examiner* — Christopher D Prone
(74) *Attorney, Agent, or Firm* — Stites & Harbison, PLLC; Juan Carlos A. Marquez, Esq

(57) ABSTRACT

The present invention is directed to a radially expandable vessel support having a multitude of annular elements flexibly connected to each other, defining a vascular support with a proximal and a distal end and a longitudinal axis. The annular elements are arranged side by side transversely to the longitudinal axis of the vascular support and connected to each other by means of bending elements. At least two marginally standing annular elements each are linked among each other by a pair of dumbbell shaped bending elements and centrally standing annular elements are linked among each other and to marginally standing annular elements by two S-shaped bending elements each, with at least the centrally standing annular elements being of a zigzag-shaped configuration.

26 Claims, 5 Drawing Sheets

U.S. PATENT DOCUMENTS 6,299,635 B1 * 10/2001 Frantzen ................ 623/1.17
6,602,281 B1 * 8/2003 Klein .................... 623/1.15

FOREIGN PATENT DOCUMENTS

| | | | |
|---|---|---|---|
| DE | 197 40 506 A1 | | 9/1997 |
| EP | 0 335 341 B1 | | 3/1989 |
| EP | 800801 A1 | * | 10/1997 |
| FR | 2 758 253 | | 1/1997 |
| WO | WO 99/17680 | | 10/1998 |
| WO | WO 99/17680 | * | 4/1999 |
| WO | WO 9917680 A1 | * | 4/1999 |

OTHER PUBLICATIONS

International Preliminary Examination Report dated Jan. 14, 2002.

* cited by examiner

RADIALLY EXPANDABLE VASCULAR STENT

The invention relates to a radially expandable vascular support to be utilized to keep blood vessels or other paths of organs open in human or animal bodies. This grid-shaped vascular support is comprised of several tubular elements with a mainly zigzag-shaped annular structure of small width, the rings of which are linked by dumbbell-shaped or S-shaped bars.

Patent EP 335 341 B1 describes vascular supports that are formed of elongated pairs of members. These vascular supports are implanted, for example, in contracted or other body vessels to keep them permanently open after a balloon dilatation. The vascular supports are thereby expanded in their diameter and contract in their lateral length. As a rule, this contraction is undesirable because it may cause a wrong positioning of the vascular support. Known vascular supports adapt themselves relatively poorly or not at all to bows or curves in the course of a vessel, thus calling for provision of additional bending elements.

Known vascular supports exhibit rigid tubular segments, which are linked to each other somewhat more resiliently through hinged connecting pieces. In these areas, however, hypertrophies of the vascular wall may occur due to the special stresses imposed on the wall on every movement of the vessel. Other known vascular supports exhibit a considerable contraction, particularly if expanded in the range of their maximum diameter.

Vascular supports with bow-shaped, equidirectional bars between zigzag-shaped annular elements, for example, are known from patent DE 197 40 506 A1. But due to numerous bars between annular elements, vascular supports of that type are very rigid and inflexible, which might involve failures when implantation is attempted in case of a curved vessel course.

On account of the numerous bow-shaped bars, it might also happen that side branches of the vascular system are unintentionally blocked, although they should remain open.

The equidirectional bow-shaped bars on the circumference also bear the disadvantage that this vascular support, in case of a curved course of the vessel, easily bends and partly or wholly blocks the vessel, which should be kept open by the vascular support.

Now, therefore, it is the task of the present invention to create a radially expandable vascular support which during its expansion is subjected to no or just a small contraction, and which bends less easily while being better suited to a curved vessel course, and which, at the same time, exhibits adequate radial stability. Likewise, in its expanded status, the vascular support should exhibit sufficiently large cross-sections between the various bars to keep lateral branches of the vascular system open.

This task for said vascular support is solved in that the vascular support exhibits a plurality of annular elements flexibly connected to each other by means of bending elements, said annular elements defining a vascular support with a proximal and a distal end and a longitudinal axis, with said annular elements being arranged side by side transversely to the longitudinal axis of the vascular support and being linked to each other by bending elements, and wherein at least two annular elements each standing at the margin are linked to each other at the proximal and distal end of the vascular support by a pair of dumbbell bending elements, and wherein annular elements standing in the center are linked among each other and with marginally-standing annular elements by two S-shaped bending elements each, with at least the centrally-standing annular elements having a zigzag shape.

Upon radial expansion of the vascular support, the bending elements stretch along the longitudinal axis, in conformity with lateral contraction of the zigzag-shaped annular elements, thus avoiding or reducing an overall contraction of the vascular support. According to the present invention, the S-shaped bars at central annular elements are arranged in pairs each, thus providing for an especially high flexibility in the central area. The S-shaped supports are expediently arranged in pairs in such a manner that they face each other on the circumference of the vascular support. The S-shaped bending elements may be arranged equidirectional or oppositely directional; because of the higher stability, preference is given to an equidirectional arrangement, but oppositely directional arrangements may also be provided for to increase flexibility.

At the proximal and distal end of the vascular support being the subject of this invention, there are two or more marginally standing annular elements each, which are linked among each other by a pair of dumbbell bending elements. These marginally standing annular elements are expediently shaped like a serpentine line, with two adjacent marginally standing annular elements expediently pointing to each other with their bows. In the area of these bows pointing to each other, on oppositely facing sides of the circumference, there are straight connecting bars of a somewhat dumbbell design. The serpentine-like design of the marginally standing annular elements in conjunction with the straight connecting and/or bending elements gives greater rigidity to the vascular support in its marginal areas that is beneficial to the stability at the vascular wall and allows for a reliable anchoring.

In the sense of the present invention, the term "dumbbell shaped" designates those bending elements, which have the shape of an upright, lying or oblique S or that of a mirror-inverted S. The term "equidirectional" means that the S-shaped or other elements on the surface of the vascular support are equally orientated in the planar representation.

Expediently the zigzag-shaped annular elements are rounded-off at their ends each to form bows. The width of the zigzag-shaped annular elements in the area of the bows may be greater than that in the area of the bars.

Furthermore, to increase stability in the various areas, particularly towards the lateral end of the vascular support, the width of the bars and/or that of the zigzag-shaped annular elements may be greater than that in other areas, particularly in the central area. On the other hand, to increase the radial force in the central area of the vascular support, the width of bars and/or bows of the zigzag-shaped elements in the central area of the vascular support may be greater than that at its ends. The various types of design each depend on the intended purpose, course of the vessel, branches of the vessel, if any, and similar factors. In this way, it is feasible to achieve broad variability with reference to adaptability and radial stability.

The vascular support which is expandable according to the present invention is expediently built-up in its central area in such a way that the zigzag-shaped annular elements are equi-directionally orientated with their bows, that means all bows point into the same direction at all levels. The same is valid for the bows of adjacent serpentine line-shaped and zigzag-shaped annular elements, thus making it possible to arrange the S-shaped bending elements diagonally staggered over the vascular support to create a spiral shape. Thereby, the vascular support has a preferred bending direction from annular element to annular element.

The S-shaped bending elements used according to the present invention at the zigzag-shaped annular elements are mainly arranged in vertical direction, that means they mainly run vertically to the bars of the zigzag-shaped annular elements. The vascular supports of this configuration thereby attain utmost flexibility. To obtain additional stability in longitudinal direction, however, it may make sense to orientate the S-shaped bending elements mainly in parallel to the bars and bows of the zigzag-shaped annular elements. Good compensation for contraction in length is thus achieved on expanding the vascular support.

The bending elements between the various annular elements preferably exhibit a somewhat smaller cross-section than the straight bar area of the zigzag-shaped annular elements, expediently by 10 to 50%, and particularly by about 30%.

Furthermore, the zigzag-shaped annular elements may exhibit different cross-sections at the edge and in the central range of the vascular support. To improve the supporting properties and radial strength at the edge, the vascular support may exhibit a larger width of the bars at both ends. To improve the local supporting properties in the area of the focal vessel narrowing and the radial strength, on the other hand, the vascular support exhibits a larger width of the bar and/or a larger cross-section in the central area only. An electro-polishing process which removes less material, for example, may achieve the larger cross-section in the central area.

The bending behaviour of the vascular support on crimping and expansion may be further improved by a particular configuration of the bows of the zigzag-shaped annular elements, for example C-shaped, or hairpin-shaped, or bracket-shaped, particularly if the width of the C-shaped or bracket-shaped bow is smaller than that of the bar of the zigzag-shaped annular element.

Preferably usable as material for the vascular support are one or more biocompatible materials of the group niobium, platinum, steel, titanium, a nickel-titanium alloy, platinum-iridium, or an alloy made from at least one of these metals like platinum-iridium with suitable weight percents. If the vascular support is to be self-expendable, a nickel-titanium alloy (Nitinol) is preferably used which is temperature-optimized by thermal treatment.

To improve the growth into the vascular wall, the metal may be coated with a biocompatible material or with suitable medicaments to avoid hyper-proliferation of the vessel, or may produce radiation by radioactive decay after irradiation or input of a radioactive material into the body or coating.

Moreover, the vascular support may be comprised of resorbable plastic material, e.g. aliphatic polyesters like polydioxanon.

If the vascular support is to be used for a splinting of aneurisms, it is preferably provided with a biocompatible fabric braided or sewn onto it, made from polyurethane, silicone, Teflon or polyester, or a thin foil made from one of these materials is sewn, welded, shrunk or glued to it.

The tubular bodies made from metal or plastic material are preferably formed from seamlessly drawn tubes in order to avoid stress and cracks, as would be the case in the vicinity of welding seams. The structures are preferably produced by laser beam cutting, water jet cutting, electro-erosion and electro-polishing.

Embodiments of the present invention are further explained in the following by way of a drawing, where:

Apart from serpentine lines, all of the vascular supports shown in these figures exhibit zigzag-shaped annular elements with S-shaped connecting elements. For clarity's sake, these figures represent the unrolled grid structures of the tube-shaped vascular supports.

Figure 1:
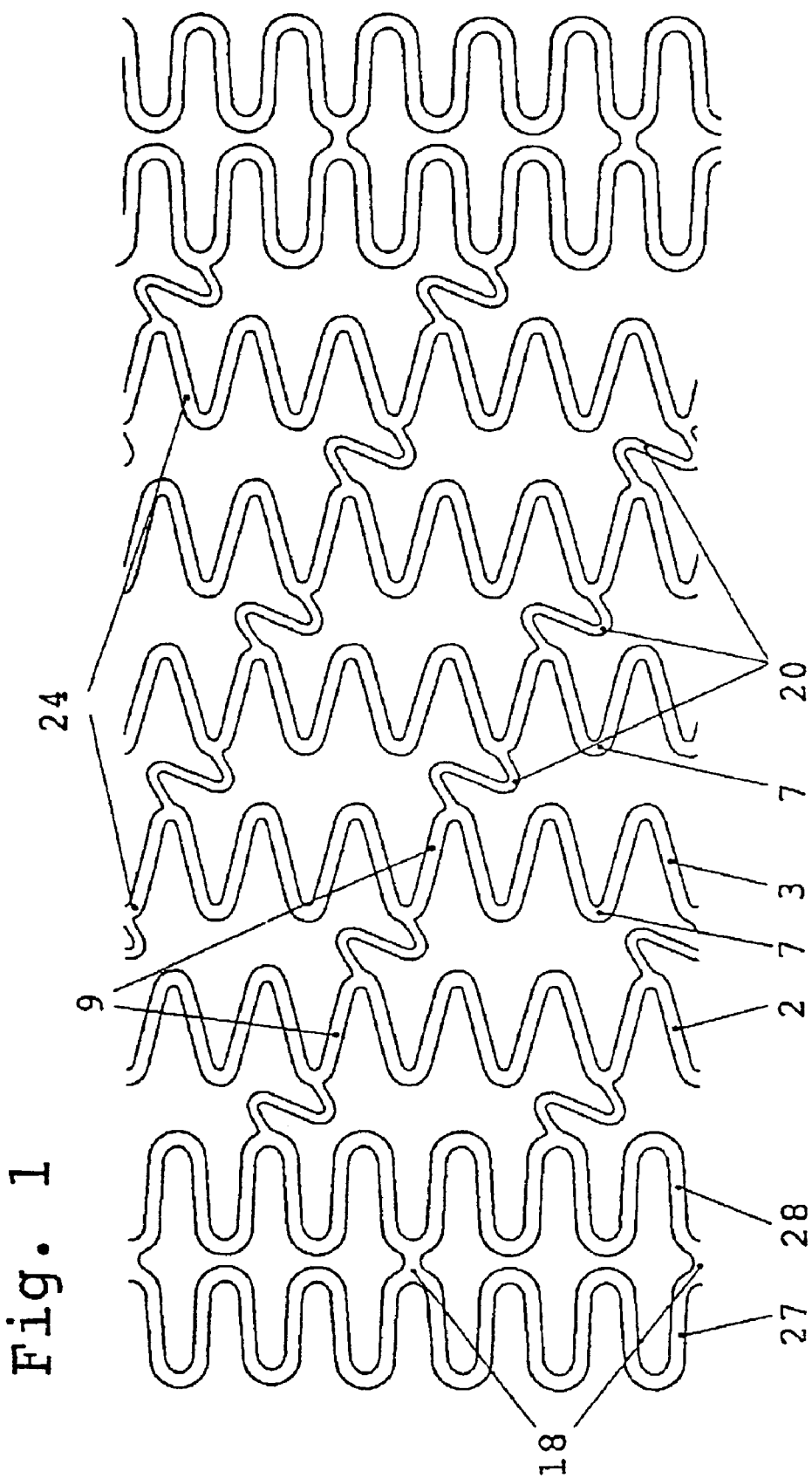
FIG. 1 shows a preferred embodiment with snake-shaped annular elements in the outer area linked by dumbbell shaped bars, and zigzag-shaped annular elements in the central area linked by more flexible S-shaped bars.

FIG. 1 shows a preferable embodiment of the invention with two snake-shaped annular elements 27, 28 each in the outer area which are linked by two dumbbell shaped bars 18 each, and zigzag-shaped annular elements 2, 3 in the central or middle area which are linked to each other by two more flexible S-shaped bending elements 20. The S-shaped bars or bending elements 20 and the zigzag-shaped annular elements 2, 3 each are arranged equidirectonally. Concerning the orientation of bows 7, 8, the annular elements 2 and 28 also run equidirectionally, while the annular elements 27 and 28 run in opposite direction.

Thus achieved is a great flexibility in the central area 24. As a peculiarity of this picture, the arches 7 of the individual annular elements 2, 3 which are open to the right, are arranged on an equal level. Upon expansion of this structure, the individual S-shaped bars 20 which will then expand, together with individual straight bars 9 lying there between and belonging to the zigzag-shaped annular elements 2, 3 form a revolving, stable double helix structure.

Figure 2:
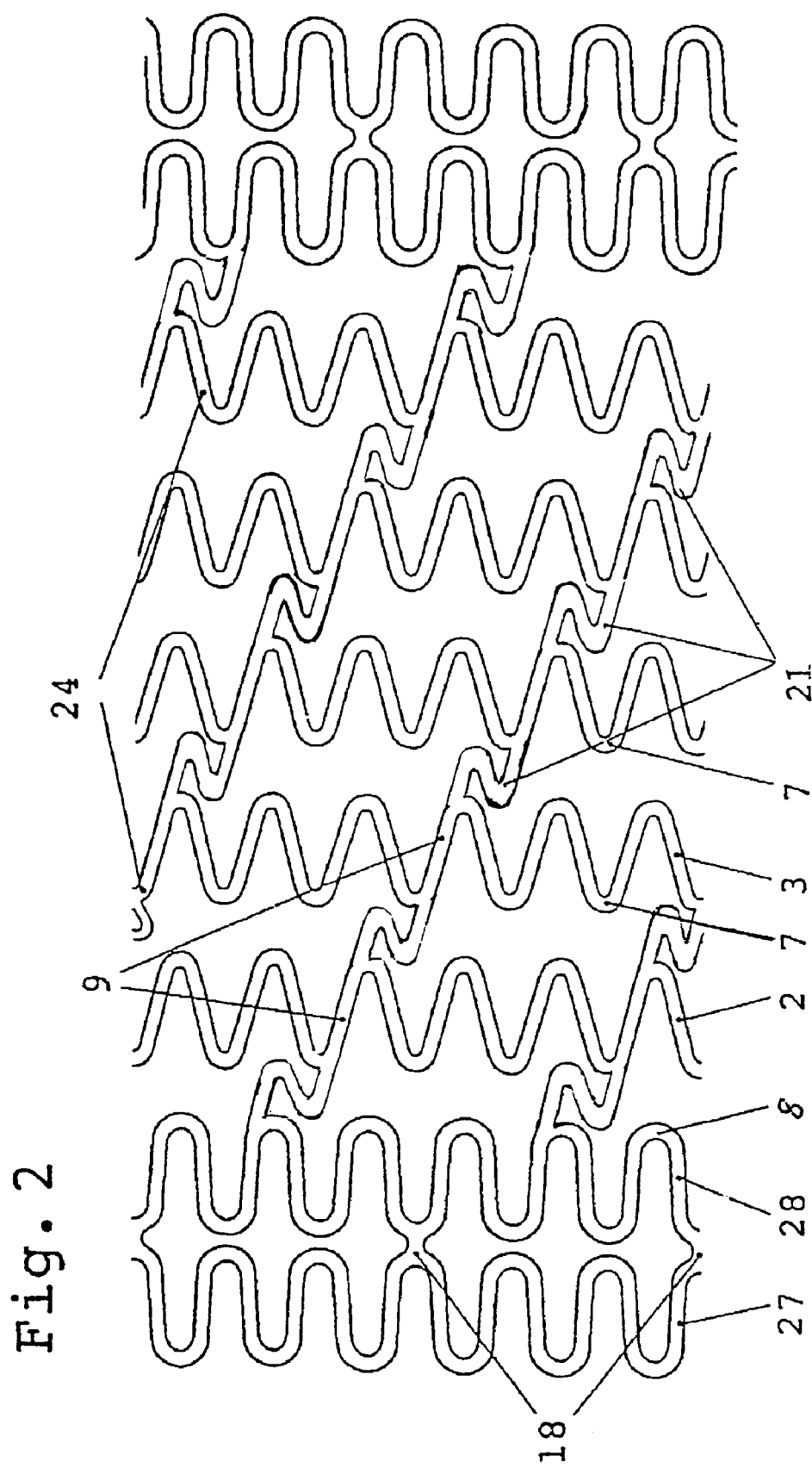
FIG. 2 shows a variant of the embodiment of FIG. 1.

FIG. 2 shows a variant of the design of FIG. 1, in which the S-shaped bending elements 21 run equidirectionally with the bars 9 and bows 7 of the zigzag-shaped annular elements 2, 3, that means the general orientation and the course of the annular elements 2, 3 in the bending elements 21 continues.

Figure 3:
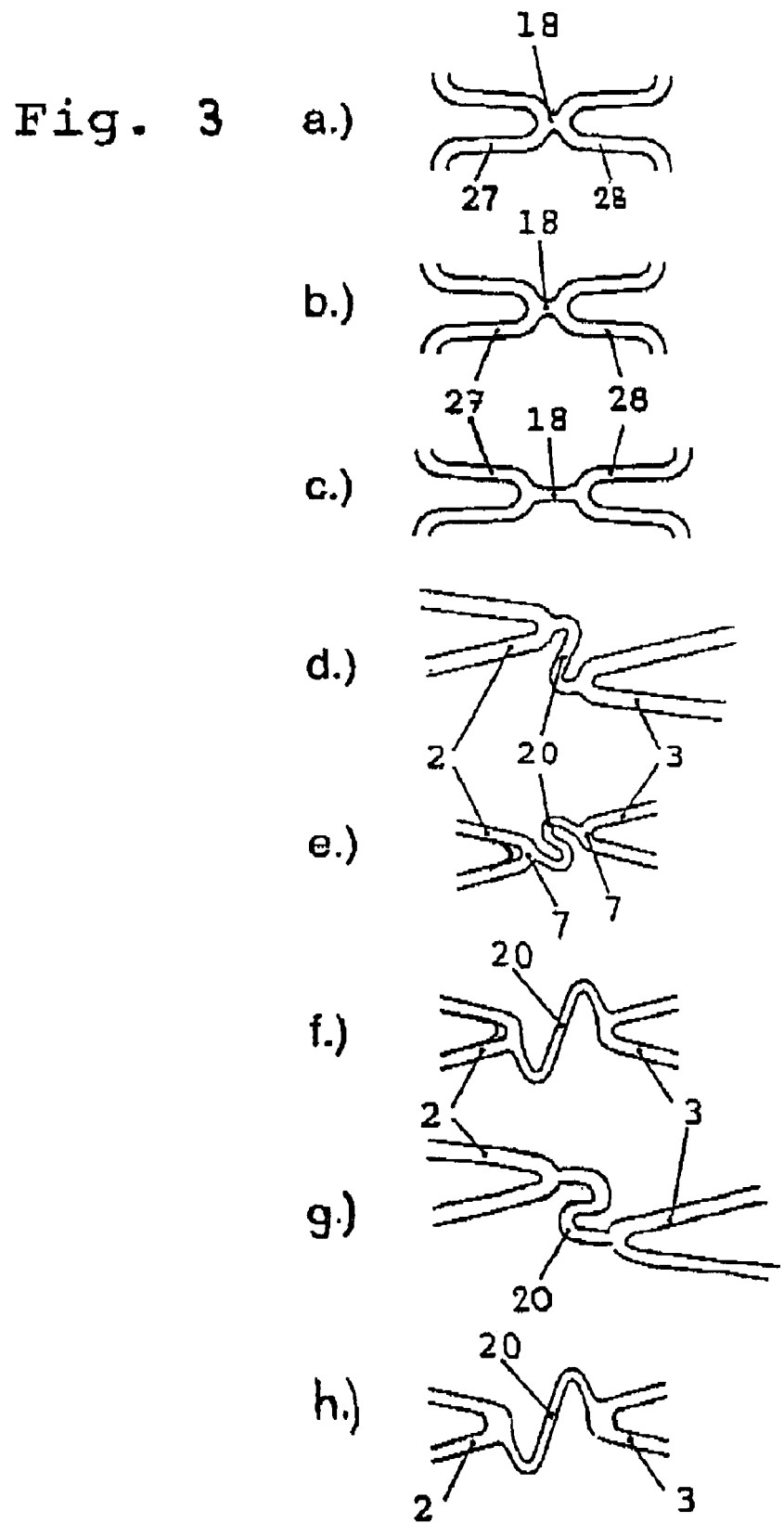
FIG. 3 shows various shapes of bending elements.

FIG. 3 shows different variants of bending elements 18, 21 and 22 that may be used. The dumb-bell shaped bending elements 18 according to (a), (b) and (c) differ by their length between the bows 8 of the annular elements 27 and 28. FIGS. 3 (d), (e), (f) and (g) show different shapes of S-shaped bending elements 20 and 21. As a matter of fact, these shapes may also be of a mirrored configuration. In FIG. 3 (h), the width of the zigzag-shaped annular elements 23 in the area of bows 7 is larger than that in the area of bars 9.

Figure 4:
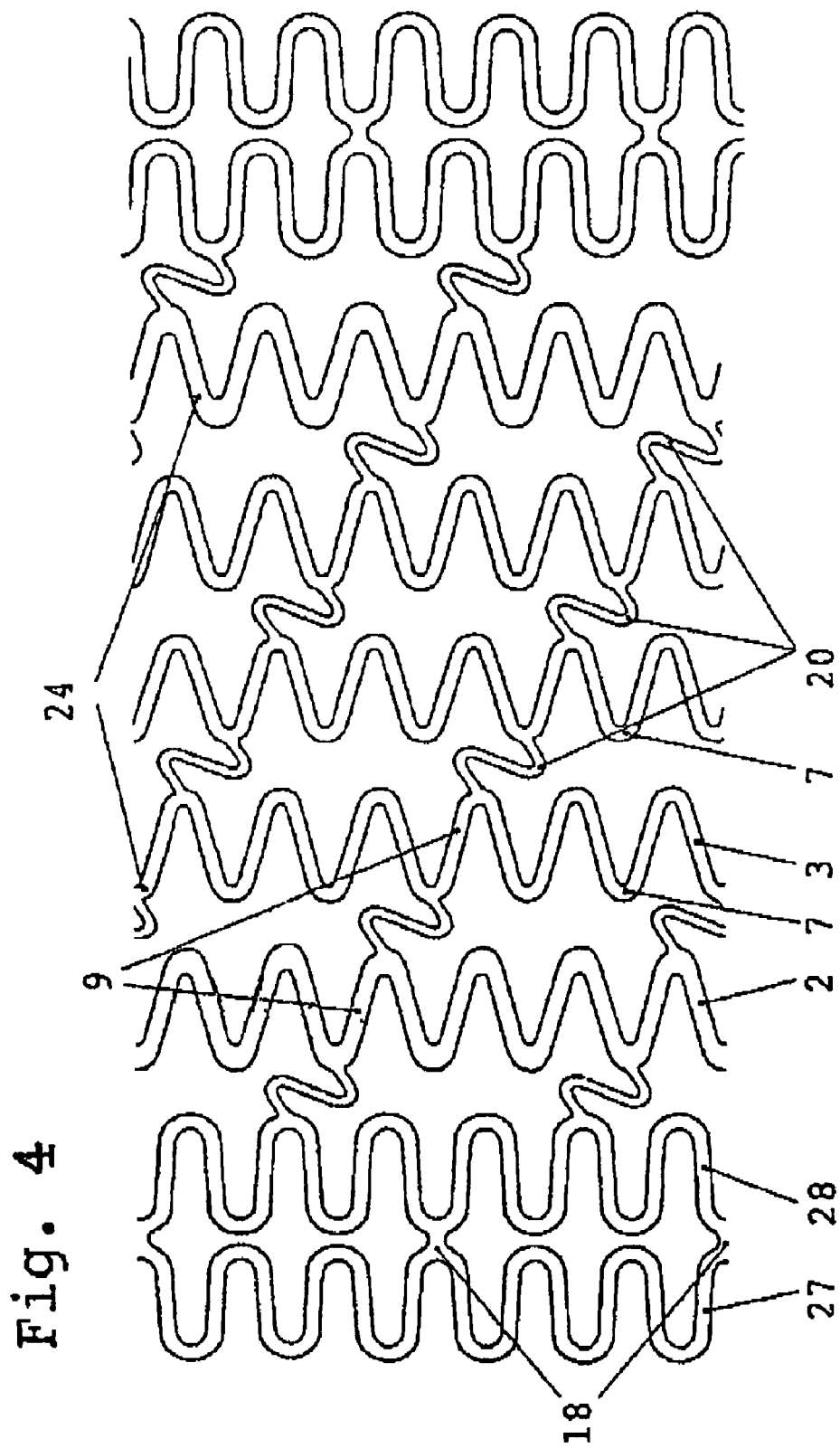
FIG. 4 shows another variant of the embodiment of FIG. 1.

FIG. 4 shows a variant of the design of FIG. 1, in which the width of bars 9 and/or bows 7 of the zigzag-shaped annular elements 2,3 at the lateral ends of the vascular support 1 is larger than that in the central area.

Figure 5:
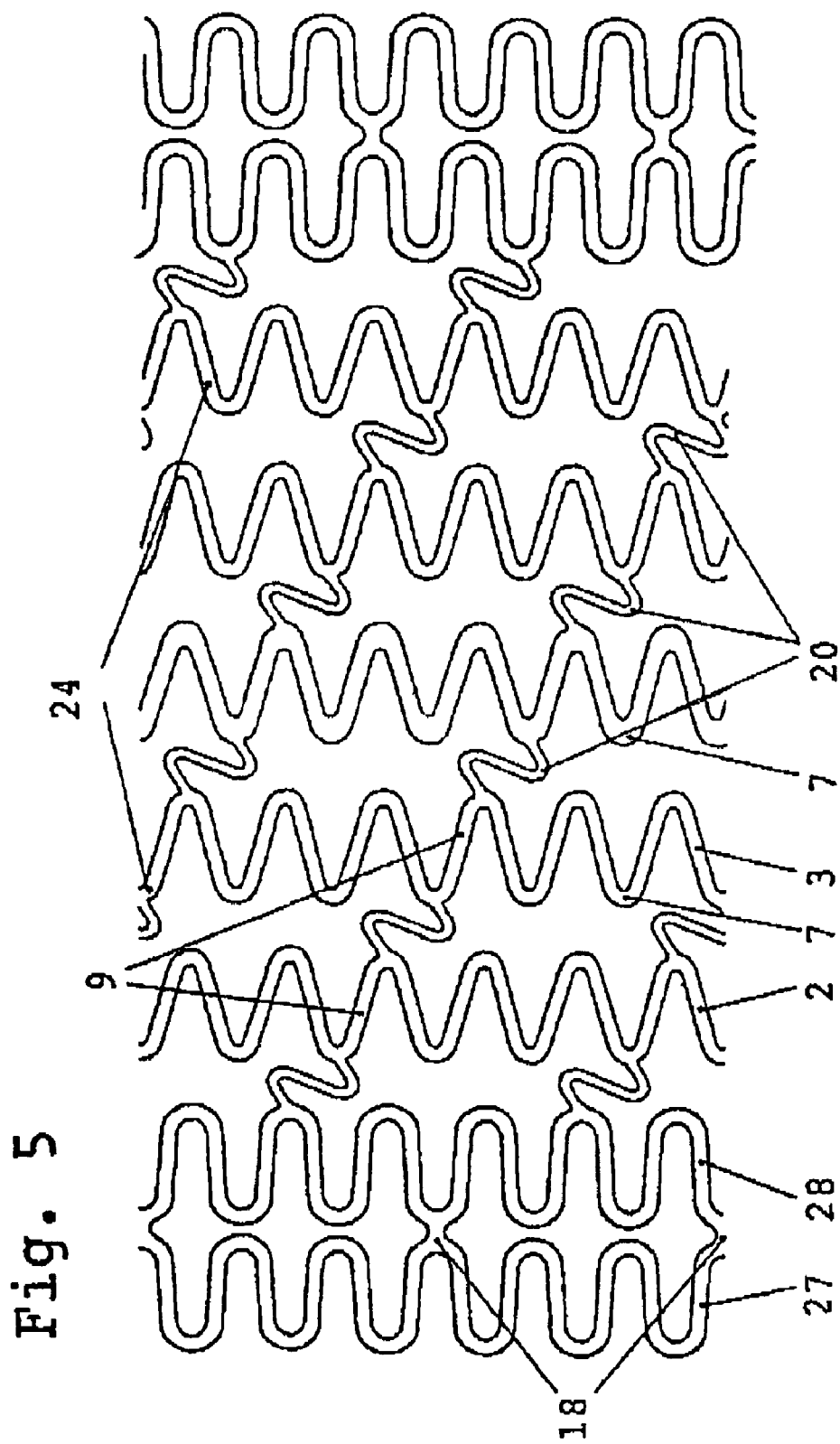
FIG. 5 shows an even further variant of the embodiment of FIG. 1.

FIG. 5 shows a variant of the design of FIG. 1, in which the width of bars 9 and/or bows 7 of the zigzag-shaped annular elements 2,3 in the central area of the vascular support 1 is larger than that at the ends.

From the above description and representation of the examples of embodiments presented it becomes evident that the present invention is not confined to the combinations of features designated in the claims or the description, but rather that within the framework of the invention, other combinations of the features specified may be conceivable.

The invention claimed is:

1. A radially expandable vessel support having a plurality of annular elements flexibly connected to each other, defining a vascular support with a proximal and a distal end and a longitudinal axis, said annular elements being arranged side by side transversely to said longitudinal axis of the vascular support, wherein
  at least two marginally standing annular elements positioned at each of the proximal and distal ends of the vascular support are linked to each other by a pair of straight bending elements, a plurality of centrally standing annular elements positioned between the marginally standing annular elements at the proximal and distal ends, each of the centrally standing annular elements being linked to each adjacent centrally standing annular element by two S-shaped bending elements only, one of the marginally standing annular elements at each of the proximal and distal ends of the radially expandable vessel support is linked to an adjacent centrally standing annular element adjacent by two S-shaped bending elements only, and each of the centrally standing annular elements is of a zigzag-shaped configuration, and wherein bending elements between two annular elements form a pair of bending elements lying opposite to each other relative to a circumference of the vascular support.

2. A radially expandable vascular support pursuant to claim 1, wherein at each of the proximal and distal ends of said vascular support, each of the two marginally standing annular elements has a serpentine line-shaped course and the straight bending elements are positioned at bows pointing to each other.

3. A radially expandable vascular support pursuant to claim 1, wherein the width of the S-shaped bending elements is by 10 to 50% smaller than the width of bars of the zigzag-shaped annular elements.

4. A radially expandable vascular support pursuant to claim 1, wherein the zigzag-shaped annular elements are rounded-off at their ends to give them the shape of a bow.

5. A radially expandable vascular support pursuant to claim 1, wherein the width of the zigzag-shaped annular elements in the area of bows is larger than that in the area of bars.

6. A radially expandable vascular support pursuant to claim 1, wherein the width of bars and/or bows of the zigzag-shaped annular elements at the lateral ends of the vascular support is larger than that in the central area.

7. A radially expandable vascular support pursuant to claim 1, wherein the width of bars and/or bows of the zigzag-shaped annular elements in the central area of the vascular support is larger than that at the ends.

8. A radially expandable vascular support pursuant to claim 1, wherein the zigzag-shaped annular elements with their bows are equidirectionally orientated.

9. A radially expandable vascular support pursuant to claim 1, wherein the S-shaped bending elements are diagonally staggered over the vascular support so as to create a spiral shape.

10. A radially expandable vascular support pursuant to claim 1, wherein the S-shaped bending elements between the zigzag-shaped annular elements are mainly arranged in vertical direction.

11. A radially expandable vascular support pursuant to claim 1, wherein the S-shaped bending elements between the zigzag-shaped annular elements are mainly orientated in parallel to said bars and bows of the zigzag-shaped annular elements.

12. A radially expandable vascular support pursuant to claim 1, wherein it is essentially made of steel, tantalum, titanium, niobium, platinum, or of an alloy consisting of at least one of these metals and at least another one of these metals or other metals.

13. A radially expandable vascular support pursuant to claim 1, wherein it is made of a resorbable material, preferably a plastic material.

14. A radially expandable vascular support pursuant to claim 1, wherein it is made of a resorbable material.

15. A radially expandable vascular support pursuant to claim 1, wherein it is coated with a biocompatible material.

16. A radially expandable vascular support pursuant to claim 1, wherein it is coated with suitable medicaments to avoid intimate hyper proliferation of the vascular wall.

17. A radially expandable vascular support pursuant to claim 16, wherein the coating slowly releases the medicaments suitable to avoid intimate hyper proliferation of the vascular wall.

18. A radially expandable vascular support pursuant to claim 1, wherein it is coated with a radioactive material, which releases a radioactive radiation to avoid or reduce hyper proliferation of the vascular wall.

19. A radially expandable vascular support pursuant to claim 1, wherein it is provided with a biocompatible fabric made of polyurethane, silicone, polytetrafluoroethylen, or polyester, or with a thin foil made of one of these materials.

20. A radially expandable vascular support pursuant to claim 1, wherein all the S-shaped bending elements are arranged in the same direction.

21. A radially expandable vascular support pursuant to claim 1, wherein a centrally standing annular element on a left of each S-shaped bending element has a right bow linking to a left bow of a centrally standing annular element on a right of each S-shaped bending element, the centrally standing annular element on the right of each S-shaped bending element has a right bow linking to a left bow of a centrally standing annular element or a marginally standing annular element adjacent to the centrally standing annular element on the right of each S-shaped bending element, the centrally standing annular element on the left of each S-shaped bending element has a left bow linking to a right bow of a centrally standing annular element or a marginally standing annular element adjacent to the centrally standing annular element on the right of each S-shaped bending element, the right bow and left bow of the centrally standing annular element on the left of each S-shaped bending element are connected via one of straight portions of the centrally standing annular element on the left of each S-shaped bending element, and the right bow and left bow of the centrally standing annular element on the right of each S-shaped bending element are connected via one of the straight portions of the centrally standing annular element on the right of each S-shaped bending element.

22. A radially expandable vessel support having a plurality of annular elements flexibly connected to each other, defining a vascular support with a proximal and a distal end and a longitudinal axis, wherein said annular elements are arranged side by side transversely to said longitudinal axis of the vascular support, and wherein at least two marginally standing annular elements positioned at each of the proximal and distal ends of the vascular support are linked to each other by a pair of straight bending elements, a plurality of centrally standing annular elements positioned between the marginally standing annular elements at the proximal and distal ends, each of the centrally standing annular elements being linked to an adjacent centrally standing annular element by S-shaped bending elements only so that each transverse distance between linked adjacent centrally standing annular elements is flexible, one of the marginally standing annular elements at each side of the radially expandable vessel support is linked to an adjacent centrally standing annular element by S-shaped bending elements only so that each transverse distance between the centrally standing annular element and the one of the marginally standing annular elements which are linked is flexible, and each of the centrally standing annular elements is of a zigzag-shaped configuration, and wherein bending elements between two annular elements form a pair of bending elements lying opposite to each other relative to a circumference of the vascular support.

23. A radially expandable vascular support pursuant to claim 22, wherein all adjacent centrally standing annular elements are linked to each other by two S-shaped bending elements only therebetween.

24. A radially expandable vascular support pursuant to claim 22, wherein one of the marginally standing annular elements at each of the proximal and distal ends of the radially expandable vessel support is linked to an adjacent centrally standing annular element adjacent by two S-shaped bending elements only.

25. A radially expandable vascular support pursuant to claim 22, wherein all the S-shaped bending elements are arranged in the same direction.

26. A radially expandable vascular support pursuant to claim 22, wherein a centrally standing annular element on a left of each S-shaped bending element has a right bow linking to a left bow of a centrally standing annular element on a right of each S-shaped bending element, the centrally standing annular element on the right of each S-shaped bending element has a right bow linking to a left bow of a centrally standing annular element or a marginally standing annular element adjacent to the centrally standing annular element on the right of each S-shaped bending element, the centrally standing annular element on the left of each S-shaped bending element has a left bow linking to a right bow of a centrally standing annular element or a marginally standing annular element adjacent to the centrally standing annular element on the right of each S-shaped bending element, the right bow and left bow of the centrally standing annular element on the left of each S-shaped bending element are connected via one of straight portions of the centrally standing annular element on the left of each S-shaped bending element, and the right bow and left bow of the centrally standing annular element on the right of each S-shaped bending element are connected via one of the straight portions of the centrally standing annular element on the right of each S-shaped bending element.

* * * * *